(12) United States Patent
Madere

(10) Patent No.: US 8,192,745 B2
(45) Date of Patent: Jun. 5, 2012

(54) NUTRITIONAL SUPPLEMENT TO IMPROVE SUPPLEMENTARY TARGET PROTEIN FRACTION (TPF) DELIVERY, INTRACELLULAR ABSORPTION AND UTILIZATION

(76) Inventor: Shawn P. Madere, Paris, KY (US)

( * ) Notice: Subject to any disclaimer, the term of this patent is extended or adjusted under 35 U.S.C. 154(b) by 0 days.

(21) Appl. No.: 12/661,481

(22) Filed: Mar. 18, 2010

(65) Prior Publication Data

US 2011/0171246 A1    Jul. 14, 2011

Related U.S. Application Data

(60) Provisional application No. 61/293,740, filed on Jan. 11, 2010.

(51) Int. Cl.
*A61K 36/05* (2006.01)
(52) U.S. Cl. .................. 424/195.17; 424/600; 424/641; 424/734; 424/757; 514/62
(58) Field of Classification Search .................. None
See application file for complete search history.

(56) References Cited

U.S. PATENT DOCUMENTS

| | | | | |
|---|---|---|---|---|
| 6,541,045 | B1 * | 4/2003 | Charters et al. | 424/737 |
| 7,416,748 | B2 * | 8/2008 | Olalde Rangel | 424/728 |
| 2005/0147675 | A1 * | 7/2005 | Petrus | 424/464 |
| 2007/0116780 | A1 * | 5/2007 | Blasi Escude | 424/602 |
| 2007/0196381 | A1 * | 8/2007 | Holt | 424/195.15 |
| 2008/0058362 | A1 * | 3/2008 | Singh et al. | 514/282 |

OTHER PUBLICATIONS

Terada (Natural Medicines (2003), vol. 57, No. 3, pp. 95-99).*

* cited by examiner

*Primary Examiner* — Susan Hoffman
(74) *Attorney, Agent, or Firm* — Stockwell & Smedley, PSC

(57) ABSTRACT

A nutritional supplement includes the primary ingredients: N-acetyl D-glucosamine, cracked cell wall Green *Chlorella*, Licorice Root Extract, and Potassium Citrate, as well as secondary ingredients: Zinc L-Carnosine, Gamma-Oryzanol and Capsaicin, that improves the bodies uptake, utilization and over-all bioavailability of exogenous target protein fractions (TPF) including but not limited to: glycoproteins, (such as glucosamine) protein isolates as amino acids, glycosaminoglycans (GAG) (including proteoglycans, and mucopolysaccharides), and polysaccharides such as hyaluronic acid (hyaluronan). The biochemical interactions of the composition improves zeta potential for TPF incorporation in the body through direct and indirect interaction with primary cellular and digestive sites of multiple species. This facilitates greater passage of target protein substrates fractions and isolates into the bloodstream, provides superior intracellular absorption and utilization thereby potentiating the therapeutic effects of TPF systemically.

18 Claims, No Drawings

NUTRITIONAL SUPPLEMENT TO IMPROVE SUPPLEMENTARY TARGET PROTEIN FRACTION (TPF) DELIVERY, INTRACELLULAR ABSORPTION AND UTILIZATION

RELATED APPLICATIONS

The present application claims priority to U.S. Provisional Patent Application Ser. No. 61/293,740 (Filed on Jan. 11, 2010), the contents of which are incorporated by reference in their entirety.

RELATED APPLICATIONS

Embodiments of the present application relate to therapeutic compositions, and more particularly, with therapeutic composition involving target protein fraction (TPF) delivery.

BACKGROUND OF THE INVENTION

Standardized complex protein chains found in food sources provide all the necessary essential and non-essential amino acid complexes, glycoproteins and glycosaminoglycans (GAG) necessary for sustained human development. Whole food proteins also provide essential and non-essential fatty acid complexes, carbohydrate chains, vitamins, and minerals. Dietary protein serves many physiological functions including cell maintenance, repair, and structure, regulation and transport of hormones, enzymes, muscle contraction, immunologic response and essential life functions.

The process by which these proteins are cleaved into specific isolates through the digestive system is well known. Throughout this process complex chains are broken down into amino acid fractions and isolates then utilized for multiple metabolic processes. Further these isolates provide the necessary building blocks for RNA and DNA development as well as forming synergistic bonds for a multitude of endogenous processes. Our further understanding of these specific protein substrates and their beneficial effects on specific tissue reparation and disease processes has led to the development and manufacture of these isolates for therapeutic use as well as dietary supplementation.

Exogenous and endogenous proteins are made from 20 essential and non-essential amino acid groups. Eight amino acids are generally regarded as essential for humans: phenylalanine, valine, threonine, tryptophan, isoleucine, methionine, leucine, and lysine. Additionally, cysteine, tyrosine, histidine and arginine are considered conditionally essential as they are required for gestation and child development. Essential amino acids are not synthesized endogenously, making it essential to include them from dietary sources. In addition, the amino acids arginine, cysteine, glycine, glutamine, histidine, proline, serine and tyrosine may also be considered conditionally essential, as they must be supplied exogenously to specific populations that do not synthesize them in adequate amounts.

Glycoproteins and glycosaminoglycans such as glucosamine, chondroitin sulfates, hepraran sulfate and hyaluronic acid are synthesized endogenously through biochemical processes and perform many regenerative functions in tissue development and repair.

Glucosamine esters were first identified as an important tissue modifier within the body in the late 1950s. This naturally occurring glycoprotein was found to be present in body tissues, with the highest concentrations present in the synovial and cartilage matrices. Trace levels are extracted from food sources and converted via digestive protein synthesis and the hexosamine glucose pathway into the active ester form glucosamine 6 phosphate. Research demonstrates the presence of glucosamine esters to have a mildly anabolic and beneficial effect on articular cartilage regeneration, by stimulating the two groups of cells responsible for cartilage maintenance and hyaluronan production: chondrocytes and synovicytes. When exposed to higher than normal levels of serum glucosamine, Chondrocytes produce more collagen, proteoglycans (the key structural matrices of fibiral, hyaline and articular cartilage) and hyaluronan (the viscous lubricant which bathes and nourishes the synovium).

Synovicytes similarly up-regulate nutrient flow and increase hyaluronic acid production. In vitro studies determine these anabolic responses are dose dependant. These findings led to the development of stabilized exogenous glucosamine forms in 1972. Their popularity as nutritional supplements has grown exponentially with the completion of multiple efficacy studies for their use in the treatment of osteoarthritis. The primary challenge for their use as a dietary supplement has been survivability of the TPF through the digestive system. Until now it has been difficult to overcome metabolic hurdles that prevent TPF delivery to serum, in high enough quantities to trigger the desired responses. The current invention is designed to enhance the bioavailability of three exogenous forms, Glucosamine HCl, Glucosamine NaCl and Glucosamine 2KCl.

Exogenous chondroitin sulfates have also gained favor as nutritional supplements for treatment of osteoarthritis due to their ability to influence tissue repair and suppress degenerative processes. When the articular cartilage becomes compromised; the chondrocytes excrete degenerative enzymes in order to remove the affected tissue so it may be replaced by healthy new cartilage. Under normal conditions this process maintains tissue equilibrium however through compressive failure, trauma or aging; an imbalance occurs and the degenerative process accelerates the onset of osteoarthritis. Chondroitin sulfate; specifically chondroitin 4-sulfate type A, has the potential to reduce the excretion of metalloproteinase, the primary degenerative enzyme inside the synovium. Chondroitin sulfates belong to the family of mucopolysaccharides, more specifically glycosaminoglycans and proteoglycans. In its purified exogenous form, chondroitin sulfate A-4 is comprised of two compounds galactosamine and glucuronic acid. The primary role of chondroitin sulfate A-4 in promoting joint health lies in the ability to reduce the degenerative enzymes metalloproteinase, bind water into the cartilage matrix and provide the basic raw material that comprises articular cartilage. It is theorized that by increasing the available pool of glycosaminoglycans via oral ingestion of chondroitin sulfate, the chondrocytes will be facilitated in their synthesis of proteoglycans thus aiding in the reparation process. This theory has proven accurate in modifying tissues and reducing clinical symptoms in both human and animal models. As chondroitin sulfates are rather large and complex molecules their metabolic fate through the digestive system has been the subject of controversy.

The use of exogenous TPF as dietary supplements has gained popularity world wide. Research science, Sports Medicine and Post-Surgical Rehabilitation have played a pivotal role in the expansive use of these isolates for both general and targeted health. Mounting clinical data demonstrates a link between the increased intake of these compounds and improvement in tissue healing, muscle hypertrophy, strength and athletic performance. Much of the data advancing the development, manufacture and use of these isolates is extrapolated from clinical trials and observations of the endogenous production and utilization of these isolates in living tissue. Unfortunately, the biochemical processes of digestion hinder and often prevent the utilization of these isolates when ingested. The problem with the bioavailability of these TPF isolates in their exogenous forms is three fold. First, the standard digestive enzymatic processes that are designed to cleave complex proteins into smaller usable isolates, expose the exogenous TPF to proteases that break-down complex biochemical bonds and denature much of the isolate. Secondly, gastric acids such as hydrochloric acid expose the isolates to extreme fluctuations in PH, that can result in mutagenic dissociations including: destruction of the TPF; conversion of the TPF into non-metabolized derivatives; and decreasing the digestibility of the TPF as a result of changes to specific rotation, isoelectric precipitation, and intra and interchain cross-linking of the TPF binding forces. Thirdly, epithelial cells of the stomach fundus, duodenum and small intestine metabolize these isolates for energy, resulting in limited survivability and subsequent limited delivery through the intestinal wall. The metabolic fate of many of these isolates is well known and demonstrated in multiple species applications. In the glycoprotein category one recent study found that only 6% of the ingested glycoprotein, glucosamine HCl and 9% of the glycoprotein glucosamine NaCl was detectable in serum after dosing. Previous radiomarker testing showed nearly 90% of this same glycoprotein was metabolized in the body, further indicating the digestive net loss for the glycopreotein through metabolic processes of over 80%. In regard to protein isolates in the form of amino acids, both animal and human studies indicate a similar reduction in the delivery to serum of the ingested compounds from about <11% to >70%. Glycosaminoglycans suffer a similar fate in uptake and utilization as evident in multiple transspecies trials at about <5% to >45%.

The separate use of some supplements to aid different metabolic functions has been used in the past. For example, N-acetyl D-Glucosamine has been included for the treatment of degenerative afflictions of the joint; as a method and agent for treating inflammatory disorders of the gastrointestinal tract; as a method for treatment of lower gastrointestinal tract disorder; and as a treatment for the prevention of interstitial cystitis.

Also, Green *Chlorella* has been used as a protective and ameliorating agent to improve Liver function, and as a preventive or therapeutic composition for viral infectious disease.

Additionally, Licorice root extracts have been used in enhanced animal food products; as a herbal composition for use in chemotherapy; as a therapeutic composition for the prevention and treatment of mucositis and mucosal disorders; as a bowel soother; a digestive aid; as a treatment for ulcers; in a composition and method for treating and preventing helicobactor-pylori-associated stomach gastritis, ulcers and cancer; and as an anti-inflammatory agent for liver function and autoimmune diseases.

Also, Potassium Citrate has been used in the treatment of autoimmune and other health disorders; prevention and treatment of hypertension; as part of a buffering agent that inhibits proton pumps and assists NSAD delivery; as part of a general health drink; in an essential nutritional drink for those with compromised digestive systems; for the treatment of osteoporosis; and as a treatment for potassium deficiencies.

Regardless of the merits of the previous research and products involving some or all of these ingredients, Applicants urge that there remains a need to combine these, and other ingredients, in a synergistic manner to improve TPF delivery.

BRIEF SUMMARY OF THE INVENTION

Embodiments of the present invention relate to a dietary supplement that includes four primary and three secondary synergistic ingredients that significantly improve TPF zeta potential, bioavailability, intracellular absorption, utilization, and therapeutic effects of exogenous TPF. These benefits include, but are not limited to classifications of: glycoproteins (such as glucosamine), protein isolates such as amino acids, glycosaminoglycans (GAG) (including proteoglycans and mucopolysaccharides), and polysaccharides such as hyaluronic acid (hyaluronan). Additionally, some embodiments favorably affect digestive biochemical responses that improve survivability and passage of TPF through the stomach resulting in higher serum levels and systemic delivery of the TPF or isolate. The four primary ingredients include: (a) N-acetyl D-glucosamine; (b) Green *Chlorella* (for example, cracked cell wall Green *Chlorella*; (c) Licorice Root Extract (for example, Licorice Root Extract 4:1); and (d) Potassium Citrate. The secondary ingredients include: (a) Zinc L-Carnosine; (b) Gamma-Oryzanol; and (c) Capsaicin.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the detailed description are to be regarded as illustrative in nature and not as restrictive.

DETAILED DESCRIPTION OF INVENTION

The detailed description set forth below is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. For example, a specific study is described herein which involved equine test subjects; however embodiments of the present invention contemplate therapeutic benefits for many different mammals including herbivores, carnivores, and omnivores.

Therapeutic compositions in accordance with embodiments of the present invention improve TPF survivability through the digestive system and deliver higher therapeutic levels of TPF to desired tissues of focus within the body. Also, in accordance with embodiments, there are synergistic relationships between the ingredients that further enhance their effectiveness and improve zeta potential for TPF. In particular, each of the ingredients N-acetyl D-glucosamine, Green *Chlorella*, Licorice Root and Potassium Citrate improve TPF survivability by satisfying specific cellular metabolic energy requirements for glycosaminoglycan and glycoprotein production; parietal, goblet and epithelial mitochondria, ATP and prostoglandin production; and catalyzing H+,K+-ATPase. As a result, TPF stores are spared from digestive energy directed metabolism, and higher than normal percentages of TPF are made available systemically. Also, TPF degradation is reduced by suppressing parietal secretions of HCl in numerous ways, including chemosensing environmental stabilization, epithelial cell sloughing, and inhibiting proton pump activity. This in-turn reduces the percentage of TPF digested within the stomach and slows proteolysis. Further, digestive pH is buffered to protect TPF integrity by reducing fluctuations in gastric acid, increasing bicarbonate secretions and increasing alkalinity on site, providing a favorable environment for TPF passage through the duodenum and small intestine.

Also, an increase in specific TPF components delivered to serum occurs including, glucosamine, GAG, and amino acid isolates. Furthermore, in accordance with the principles of the present invention, TPF delivery is potentiated and incorporated systemically through reductions in oxidative stresses, and anti-inflammatory pathways. Although benefits are provided by the individual ingredients, however, when used in combination the net result has been clinically proven to be statistically greater than that realized by the individual application alone.

Embodiments of the present invention provide an all natural nutritional supplement that improves the body's uptake, utilization and over-all bioavailability of exogenous, target protein fractions (TPF) including but not limited to; glycoproteins, protein fractions and isolates (amino acids) and glycosaminoglycans (GAG—including proteoglycans and mucopolysaccharides). Upon entering the stomach TPF isolates (including glycoproteins, amino acids and GAGs) stimulate hormonal responses that trigger the release of gastric acids that are designed to breakdown complex proteins. Unfortunately this cascade of HCl acid pepsin and gastric acids prematurely denature these isolates and prevent efficient delivery through the digestive system. Embodiments described herein facilitate greater passage of TPF into the bloodstream of multiple species by direct and indirect interaction with primary digestive and metabolic sites, including stomach, duodenum and small intestine. Mechanisms of action include: physiological and biochemical changes in cell signaling, hormone secretion, digestive juice secretion, digestive pH and cellular and mucosal metabolism of TPF. Synergistic relationships between the ingredients protect TPF integrity, prevent oxidation, slow proteolysis and balance biochemical relationships necessary for optimal utilization of TPF systemically. Through these physiological and biochemical mechanisms, molecular degradation is slowed or prevented resulting in a higher percentage of the ingested TPF surviving passage through the digestive tract than has otherwise been possible. This improves the zeta potential of the TPF and allows a higher percentage of the TPF to be made available for endogenous metabolism at multiple sites throughout the body. By mildly altering the body's digestive processes for multiple species in favor of TPF survivability and improving TPF delivery, embodiments described herein increases therapeutic potential for TPF.

Embodiments of the present invention relate to a dietary supplement that includes four primary and three secondary synergistic ingredients that significantly improve TPF zeta potential, bioavailability, intracellular absorption, utilization, and therapeutic effects of exogenous TPF. These benefits include, but are not limited to classifications of: glycoproteins (such as glucosamine), protein isolates such as amino acids, glycosaminoglycans (GAG) (including proteoglycans and mucopolysaccharides), and polysaccharides such as hyaluronic acid (hyaluronan). Additionally, some embodiments favorably affect digestive biochemical responses that improve survivability and passage of TPF through the stomach resulting in higher serum levels and systemic delivery of the TPF or isolate. The four primary ingredients include: (a) N-acetyl D-glucosamine; (b) Green *Chlorella* (for example, cracked cell wall Green *Chlorella*; (c) Licorice Root Extract (for example, Licorice Root Extract 4:1); and (d) Potassium Citrate. The secondary ingredients include: (a) Zinc L-Carnosine; (b) Gamma-Oryzanol; and (c) Capsaicin.

The amount of primary and secondary ingredients in the dietary supplement can be varied depending on the intended target. For example, herbivores, carnivores, and omnivores all can have different dosing ranges to maximize the benefits of embodiments of the present invention. In terms of dosing, it is common to normalize the measurements of ingredients by specifying a per unit dosage. For example a dosing amount can be specified as 75 micrograms per kilogram of body weight and written 75 mcg/kg. Thus, if the per unit was "kilograms", then the per unit dosage would be 75 mcg. One of ordinary skill will recognize that dosing amounts may be specified in other formats without departing from the scope of the present invention.

Embodiments of the present invention include the ingredients described above, wherein the ingredients are available in species dependent dosing within the following categories and ranges:

| | AVAILABLE DOSING | | |
|---|---|---|---|
| Ingredient | Herbivore | Carnivore | Omnivore |
| N-acetyl D-glucosamine | 750 mcg/kg to 7.5 mg/kg | 3 mg/kg to 30 mg/kg | 6.9 mg/kg to 69 mg/kg |
| Green Chlorella | 450 mcg/kg to 4.5 mg/kg | 1.8 mg/kg to 18 mg/kg | 4.1 mg/kg to 41 mg/kg |
| Licorice Root Extract | 188 mcg/kg to 1.88 mg/kg | 1.8 mg/kg to 18 mg/kg | 1.7 mg/kg to 17 mg/kg |
| Potassium Citrate | 10 mcg/kg to 100 mcg/kg | 20 mcg/kg to 200 mcg/kg | 46 mcg/kg to 460 mcg/kg |
| Zinc L-Carnosine | 188 mcg/kg to 1.88 mg/kg | 1.8 mg/kg to 18 mg/kg | 1.7 mg/kg to 17 mg/kg |
| Gamma-Oryzanol | 600 mcg/kg to 6 mg/kg | 6 mg/kg to 60 mg/kg | 6 mg/kg to 60 mg/kg |
| Capsaicin | 10 mcg/kg to 1 mg/kg | 400 mcg/kg to 4 mg/kg | 10 mcg/kg to 1 mg/kg |

Discussion of Individual Ingredients:

N-Acetyl D-Glucosamine:

N-Acetyl D-Glucosamine is a derivative of glucose obtained by chemical hydrolysis of chitin. It is an amide between glucosamine and acetic acid. It has a molecular formula of a molar mass of 221.21 g/mol, and it is significant in several biological systems. This monosaccharide is unique in the exogenous glucosamine family as it is available in the ester form and does not require cleaving of an anion or cation carrier in order to be metabolized by the body. This property allows N-acetyl D-glucosamine to work directly with cellular mucosa, specifically secreting cells of the buccal, fundal, and endothelial wall. In the exogenous form it is readily soluble in water and extremely bioavailable.

Previous studies on the metabolic fate of exogenous N-acetyl D-glucosamine indicate N-acetyl D-glucosamine provides one of the primary structural components of all mucosal surfaces and is directly incorporated into both stomach and intestinal mucosa. Exogenous N-acetyl D-glucosamine is also rapidly metabolized within the mucosal lining and directly incorporated as substrates for tissue repair in the manufacture of endogenous glycosaminoglycans and glycoproteins. Under normal digestive processes the epithelial cells of the stomach utilize TPF through metabolic pathways for the production of these substrates. As a result, this reduces the percentage of TPF available for passage into the duodenum, small intestine and circulation to desired tissues within the body. By rapidly satisfying the immediate energy requirements of epithelial cells, N-acetyl D-glucosamine provides a mechanism that is unique in the ability of an orally administered glycoprotein to prevent excessive TPF metabolism in the stomach. Further, there are biochemical interactions with gastric inflammatory processes that contribute to TPF survivability through the gastric mucosa and the epithelium. N-acetyl D-glucosamine has been shown to reduce inflammation in mucosal surfaces by suppressing histological triggers that produce excessive nitric oxide (NO) via cellular TNF.ALPHA. and IL-1.BETA. inflammatory responses. Endogenous NO is involved in mucosal defense by partially decreasing HCl secretion, however excessive NO catalyzes peroxynitrite formation, increases cellular toxicity and increases acidic responses that denature TPF. N-acetyl D-glucosamine is unique in this regard as a regulator of NO production as it does not interfere with normal IL-1.BETA inhibitory effects on gastric acid secretion. Lastly, N-acetyl D-glucosamine acts as an intermediary for other exogenous forms of glucosamine through the stomach. The rapid incorporation of N-acetyl D-glucosamine by epithelial cells in the fundus satisfies the primary glucosamine metabolic necessity and allows up to four times greater passage of D-glucosamine forms into serum. Within the scope of the present invention N-acetyl D-glucosamine facilitates and improves the bioavailability of TPF through a variety of direct and indirect biochemical actions, including: preventing premature TPF incorporation in the stomach by satisfying primary metabolic sites for endogenous GAG and glycoprotein production; stabilizing biochemical reactions that provide greater opportunity for predigested protein fractions to survive denaturing; and directly facilitating TPF passage through the stomach by mediating epithelial cell metabolism.

Broken Cell Wall, Green *Chlorella:*

*Chlorella Pyrenoidosa* and *Vulgaris* are a unicellular microalgae, grown in fresh water. *Chlorella* is a prime food supplement in Japan and other Far East countries and is considered a "functional nutrient" in Europe due to its rich nutritive value. *Chlorella* contains very high levels of chlorophyll, protein, carotanoids; including astaxanthin, canthastaxanthin, flavoxanthin, loraxanthin, neoaxanthin, and violaxanthin. Active ingredients of *chlorella* are: 61.6% protein, 12.5% fat, 13.7% carbohydrate, trace elements (Al, Ze, P, Ca, Mg, Mn, Ni, Se), vitamins (carotene, beta-carotene, thiamine, B1, B2, B6, C, D, E, K), nucleic acids (RNA and DNA), and various enzymes including the digestive enzyme pepsin. Common chlorella without special treatment is hard to digest as the cellular wall prevents the release of stored nutrients. Traditionally, the digestibility rate is less than 40%. Biotechnological processing can improve digestibility with low-pressure flash expansion, also known as "broken cell process", in which the cell wall is exposed to high pressure and temperature changes that reveals numerous pores within the cell wall without damaging or denaturing the active ingredients. This process improves digestibility and bioavailability to greater than 80%. *Chlorella* has been studied as an effective treatment for intestinal adaptation in SBS. *Chlorella* also demonstrates putative hypolipidemic and gastro mucosal-protective activities as well as up-regulating and improving glycogenesis; receptor binding for amino acids as well as prevention of osteoporosis. The multiple functions of *chlorella* in relation to digestion, mucosal protection, protein and lipid regulation provide beneficial results in embodiments of the present invention.

*Chlorella* has the unique ability to influence multiple physical and biochemical processes that simultaneously reduce denaturing and enhance the body's utilization of TPF. Direct interaction of *Chlorella* on mucosal and intestinal membranes in SBS demonstrates specific biochemical changes that provide beneficial results. In a study described below, the addition of *chlorella* produces a significantly higher percentage of amino acid delivery to serum 68.8% for *chlorella* verses 34.2% for control. In the same study, accelerated physical changes in villus lengthening, crypt depth, mucosal DNA, and intestinal proliferation were realized. Serum citrulline, protein and albumin levels were found to be significantly higher in those receiving *chlorella* than those in the control group further indicating chlorella's protective role in protein isolate survivability. Much of the attributable benefits for improved amino acid and protein fraction delivery to serum relates to the metabolic fate of *Chlorella*. Upon entering the stomach *Chlorella* provides a complete and stable metabolite for mucus secreting goblet cells as well as the energy dependent mitochondria of parietal and epithelial cells. In turn this stable environment prevents rapid biochemical fluctuations within the fundus that produce excess parietal gastric acid secretions that break down peptide bonds. This stabilization also helps reduce HCl secretion that subjects protein fractions to extremely low pH conditions that denature TPF. In turn the active metabolism of *Chlorella* by the epithelial cells also reduces the de-stabilizing effect of excessive bicarbonate secretion or "alkaline tide" caused by sudden changes in protein sensing that occur in gestation, and prevents excessive fluctuations in gastric pH. By controlling swings in luminal chemosensing, *Chlorella* helps regulate digestive secretion fluctuations and improves TPF survivability. This has been demonstrated by the prophylactic effect of *Chlorella* in stress-induced and in cysteamine-induced peptic ulcer models. *Chlorella* has also been shown to promote optimal digestive processes in regulating GAG and fatty acid and glucose metabolism and was found to have inhibitory binding effects on specific amino acids receptors in endothelial cells. Within embodiments described herein *Chlorella* proves to be a stable metabolite, effective in reducing HCl secretion, reducing pH fluctuations, preventing proteolysis and improving TPF incorporation in the body. The aforementioned mechanisms and protective activities of *Chlorella* on gastric mucosa, potentiates *Chlorella* as a prime catalyst in amino acid and glycoprotein survivability and passage through the digestive system. Further the effect of *Chlorella* on intestinal adaptation, and normalizing the biochemical processes that improve TPF digestive efficiency are benefits of at some embodiments described herein.

Licorice Root Extract:

The roots of licorice (*Glycyrrhiza*) have long been used worldwide as a herbal medicine and natural sweetener. A large number of components have been isolated from licorice, including triterpene saponins, flavonoids, isoflavonoids and chalcones, with glycyrrhizic acid normally being considered to be the main biologically active component. Other constituents include, flavonoids; liquiritin, liquiritigenin, rhamnoliquiritin, neoliquiritin, chalcones isoliquiritin, isoliquiritigenin, neoisoliquiritin, licuraside, glabrolide and licoflavonol, 5,8-dihydroxy-flavone-7-O-beta-D-glucuronide, glychionide A, and 5-hydroxy-8-methoxyl-flavone-7-O-beta-D-glucuronide, glychionide B. Isoflavonoid derivatives present in licorice include glabridin, galbrene, glabrone, shinpterocarpin, licoisoflavones A and B, formononetin, glyzarin, kumatakenin, hispaglabridin A, hispaglabridin B, 4_-O-methylglabridin and 3_-hydroxy-4_-O-methylglabridin and glabroisoflavanone A and B glabroiso-flavanone B have been found. Coumarins present in licorice root include, liqcoumarin, glabrocoumarone A and B, herniarin, umbelliferone, glycyrin, glycocoumarin, licofuranocoumarin, licopyranocoumarin and glabrocoumarin. Four new dihydrostilbenes have recently been discovered as well including; dihydro-3,5-dihydroxy-4_-acetoxy-5_-isopentenylstilbene, dihydro-3,3_,4_-trihydroxy-5-O isopentenyl-6-isopentenylstilbene, dihydro-3,5,3_-trihydroxy-4_-methoxystilbene and dihydro-3, and 3_-dihydroxy-5beta-d-O-glucopyranosyloxy-4_-methoxystilbene. Licorice root also contains fatty acids (C2-C16) and phenols (phenol, guaiacol), together with common saturated linear _-lactones (C6-C14). A series of new 4-methyl-_-lactones and 4-ethyl-_-lactones in trace amounts has also been found. Asparagines, glucose, sucrose, starch, polysaccharides (arabinogalactants), and sterols (_-sitosterol, dihydrostigmasterol) are also present. Licorice isoflavans are partly incorporated into the body in an unchanged form, though most of the dietary flavonoids are converted to non-active conjugate forms during intestinal absorption. It is the capacity of licorice root and its constituents to influence digestive processes provide benefits in accordance with the principles of the present invention.

Licorice root extracts have been extensively studied for the treatment of peptic ulcer, hepatitis C, and pulmonary and skin diseases, although clinical and experimental studies suggest that it has several other useful pharmacological properties such as anti-inflammatory, antiviral, antimicrobial, antioxidative, anticancer activities, immunomodulatory, hepatoprotective and cardioprotective effects. In accordance with embodiments of the present invention, of greater interest are the interactions of licorice root on stomach gastric secretions, mucosal production and epithelial and parietal cellular metabolism, intestinal mucosa secretions and heptatic interaction that potentiates TPF systemic availability. These biochemical changes elicited by licorice root and its constituents, improve the zeta potential and facilitate greater uptake of TPF to serum and greater delivery to target metabolic sites in the body. Licorice root extracts have a direct modulatory affect on digestive signaling hormones, specifically inhibiting the release of gastrin by parieterial cells in both the stomach and duodenum and increasing bicarbonate secretion. Through this mechanism licorice reduces the acid secretion that is triggered by the arrival of TPF to the stomach reducing proteolysis and improving TPF survivability. The subsequent increase in bicarbonate helps neutralize the pH of the digestive secretions in both the stomach and duodenum, preventing further proteolysis and improving survivability and delivery of TPF to the small intestine. Zeta potential of TPF to serum is also improved by reducing the catabolic and digestive metabolism of TPF by active cells in the stomach. Both mucus secreting epithelial cells and HCl secreting parietal cells use TPF for energy in producing adenosine triphosphate (ATP) to transport H+ across the cell membrane into the gastric lumen and potassium ions (K+) in the opposite direction. Licorice is effective in reducing the cellular metabolism of TPF by raising the local concentration of prostaglandins within the stomach. In turn the epithelial cells secrete excess mucus as well as bicarbonate to protect the underlying stomach. Not only does this process slows HCl secretion by parietal cells and slightly raise the Ph of pepsin, thereby reducing TPF digestion, but the increase of prostaglandins, triggers cellular proliferation and sloughing of the epithelial cells thereby reducing the necessity for ATP production. By reducing the metabolic utilization of TPF for ATP within the stomach more therapeutic composition is provided to serum. Licorice also potentiates TPF delivery systemically through antioxidant and anti-inflammatory pathways. Exposure to oxidative stress is one of the primary inhibitors of amino acid importation, metabolism, and assimilation into all cellular endoplasmic reticulum and there is a clear correlation between the reduced exposure to oxidative stress and proper cellular function. Licorice constituents have proven highly effective at reducing oxidative stress systemically, and most notably in attenuating atherosclerosis through a high antioxidative capacity toward LDL oxidation. Reducing cellular oxidation further facilitates proper utilization of TPF in the body. Inflammatory processes present additional challenges to TPF utilization. Several inflammatory pathways contribute to a reduction in systemic cellular protein metabolism and intercellular synthesis. Cytokines including IL-6 and TNF-alpha, fibrinogen, _2-macroglobulin and albumin, are primary contributors to the effects of inflammation on reduced muscle protein metabolism. Studies have shown a direct correlation between these cytokines and poor TPF incorporation. Licorice and its constituents are considered as anti-inflammatories for multiple disease processes, and have proven to be effective in inhibiting protein blocking cytokines IL-6, TNF-alpha, and reducing the production of inflammatory mediators such as nitric oxide (NO) as well as myeloperoxidase, prostaglandin (PG) E2, and the inflammatory enzyme phospholipase A2. Embodiments of the present invention rely on benefits of this anti-inflammatory mechanism in facilitating optimal TPF incorporation and synthesis. Another benefit of licorice, according to embodiments, is in improving TPF survivability and zeta potential through multiple biochemical mechanisms including: modulating digestive signaling hormones, suppressing gastric acid secretions, increasing gastric pH, reducing stomach TPF metabolism and ATP conversion through increased prostoglandin and epithelial sloughing, and potentiating systemic TPF incorporation by reducing oxidative stresses.

Potassium Citrate:

Potassium (K) is an essential alkali mineral macronutrient with a wide range of biochemical and physiological roles. Potassium is also classified as an electrolyte as it dissociates into ions in solution. It is biologically important in the transmission of nerve impulses, muscle contraction, energy production, synthesis of nucleic acids and maintenance of intracellular tonicity. Many foods are good sources of potassium including, fresh fruits and vegetables, fish meats and cheeses. Normal body function depends on tight regulation of potassium concentrations both inside and outside of cells. In healthy mammals, approximately 98% of the body's potassium is stored in intracellular fluids, and 2% in the extracellular environments. Potassium citrate is a citrate salt of potassium. Its empirical formula is $K_3 C_6 H_5 O_7 \cdot H_2 O$ and is rapidly absorbed orally. Currently supplemental potassium citrate is recommended for cases of diuretic induced hypokalemia, hypertension, as well as cerebrovascular and cardiovascular-protective activities.

Potassium possesses multiple biochemical activities that are beneficial for embodiments of the present invention. One of the most vital and well understood is the sodium, potassium-ATPase pump (Na+,K+-ATPase). Potassium is the principal positively charged cation inside cells, while sodium is the principal cation in extracellular fluids. The concentration differences between potassium and sodium across cell membranes create an electrochemical gradient known as the membrane potential that utilizes energy from ATP for ion exchange. Regulating this potential through dietary potassium is vital for sustaining life. Maintaining the proper ratios of potassium within the body ensures optimal uptake of TPF, cellular nutrients and waste removal systemically. More importantly it has been demonstrated that gastric potassium interacts directly with secretory tissues of the gastric lining including: the basolateral membrane of parietal cells, apical surface membranes, secretory canalicular membranes and tubulovesicles. Potassium is a cofactor for gastric lumen proton pump activation. The gastric H+,K+-ATPase exploits a very similar enzymatic mechanism to catalyze the electroneutral exchange of intracellular protons for extracellular potassium ions, thus generating the enormous proton gradients associated with gastric acid secretion. The proton pump consists of an enzyme reaction in the parietal cell membrane that uses ATP to transport H+ across the cell membrane into the gastric lumen and potassium ions (K+) in the opposite direction. This mechanism releases HCl for pepsin activation as well as bicarbonate to protect the immediate tubular structures from HCl. The activation of the pump is regulated in the parietal cell membrane by a combination of gastric stimuli including, the proper pH, acetylcholine, histamine and gastrin, which act on the muscarinic, and histamine and gastrin receptors. The presence of extracellular potassium is vital for activation, and fluctuations in potassium content directly affect proton pump activation. Exogenous potassium citrate helps reduce TPF digestion by interacting directly with luminal digestive secretions to reduce the production of HCl and the activation of pepsin in the following manor. As these mechanisms require an acidic environment of 4.0 or lower for activation, the alkaline properties of extracellular potassium citrate temporarily raises gastric pH to levels that inactivate the H+,K+ATPase-gastric acid pump. Unlike PPI drugs omeprazole, lansoprazole, and pantoprazole that suppress this activity for durations of 2 hours or more, potassium citrate only inhibits this activity while present in gastric concentrations. This buffering contributes to the neutralization of the protein-induced metabolic acidosis in the stomach and allows more intact TPF to pass through the stomach in tandem undigested thereby improving zeta potential as well. In addition, the passage of alkaline potassium citrate returns gastric pH to levels below 4.0 upon emptying of the embodiment into the duodenum. Upon entering serum, potassium citrate continues to aid in TPF utilization and metabolism by further neutralizing protein-induced metabolic acidosis systemically. It has been demonstrated that through this mechanism the addition of dietary potassium citrate facilitates cellular incorporation of TPF, prevents muscle-protein wasting, improves basolateral membrane protein metabolism, and reduces oxidative stress. The addition of potassium citrate within embodiments of the present invention also works synergistically with supplemental licorice in preventing the possibility of sodium imbalances or hypokalemia related to licorice supplementation, making the use of potassium citrate supplementation beneficial as a co reactive for balancing Na/K ratios. Embodiments of the present invention contemplate the application of dietary potassium citrate, specifically for the improvement of TPF incorporation through the following mechanisms: temporarily increasing gastric alkalinity, raising gastric pH, reducing HCl secretions via proton pump inactivation, buffering digestive acidosis, and improving zeta potential by providing a more favorable pH for TPF emptying to the duodenum. Embodiments as contemplate the application of potassium citrate as a cofactor for ionic stabilization in relation to licorice induced hypokalemia.

Although the above ingredients provide benefits individually or in blends that do not involve all four ingredients, the blend of the four primary ingredients provides synergistic benefits over the individual components. In addition, one or more secondary ingredients can be included to provide additional benefits as well. For example, selecting one or more of the following ingredients for inclusion (a) Zinc L-Carnosine; (b) Gamma-Oryzanol; and (c) Capsaicin provides particular benefits.

As mentioned above, embodiments of the present invention were used in a clinical trial to study the therapeutic results of various compositions. The clinical trial is described more fully below:

Clinical Trial

Case Study 1: Embodiments of the present invention are designed to improve the therapeutic potential for TPF incorporation in the body. This beneficial result is achieved through synergistic biochemical interactions and catalytic responses that improve the zeta potential of TPF; provide greater passage of TPF to serum; improve intracellular absorption and utilization of TPF; and potentiate the therapeutic effects of TPF throughout the body. The biochemical and physiological interactions of embodiments of the present invention have been evaluated in a 6-month, randomized, control group, multi-centre efficacy study to test the hypothesis in Equine. The study was designed to test bioavailability, cellular interaction, safety and the potentiation of therapeutic action of embodiments in vivo.

An example TPF chosen for the study includes a blend of exogenous glucosamine HCl, glucosamine NaCl, glucosamine 2KCl and chondroitin sulfate. This TPF blend is a commercially available product with the trade name GLC 5500. This TPF blend has been used in previous peer reviewed equine clinical trials at a recommended rate of 1000 mg. per pound of bodyweight and has demonstrated efficacy in the treatment of osteoarthritis. In vivo testing of the TPF, GLC 5500 in equine has clinically established a bioavailability of <30% as determined by serum evaluations using the industry standard testing methods of HPLC and DMMB for glucosamine, glycoprotein and glycosaminoglycans. Embodiments of the present invention were added to the original GLC 5500 product and extensively studied for a 6 month period. The details of the current trial are divided into two subheadings as follows:

Purpose of the Study:

SUBHEADING-A: To evaluate the pharmacokinetics, serum bioavailability and effect on synovial fluid concentrations of GLC 5500 with the addition of embodiments of the present invention as compared to previous TPF bioavailability findings on GLC 5500 alone as well as control.

SUBHEADING-B: To evaluate the physiological effect of GLC 5500 with the addition of embodiments of the present invention on AAEP lameness scores as well as TPF safety related to cellular bio-availability Hematologic, hemostatic and uptake response.

SUBJECTS—75 equines

STUDY TYPE—6-month, Randomized, Control Group, Multi-Centre Efficacy Study

SUBHEADING-A, PROCEDURES—Equines were selected from a large population of high performance chronic joint pain/limited ROM sufferers as determined by veterinarians. The subjects were randomized into two groups of subjects. The 50-subjects in Group A were provided GLC 5500 with the addition of embodiments of the present invention and administered 5.63 grams of the composition BID day with regular feedings. (1-full scoop of combined products in the morning and 1-full scoop in the evening grain rations.) Subjects in Control Group B were fed normal rations without the addition of any secondary nutritional supplements or placebo to establish control. Blood and synovial fluid samples were collected and evaluated at baseline, and 4 week intervals thereafter. Blood samples were assayed using (HPLC and DMMB) to determine serum bioavailability for TPF-glucosamine and glycoproteins and total chondroitin sulfate as measured in total GAG content. Bioavailability data from both groups was compared using standard statistical mathematical calculations to identify effects of treatment. Synovial fluids were taken from the tarsus of 40 equines in Group A and tested using 10 specific biochemical markers including, total protein, Hyaluronan, Albumin, Glucose, Sigma, LDH, Sibley-Lehiniger, Sigma-Frankelunits (units/ml and Sigma-Frankelunits/ml) and Glutamic pyruvic transaminaseactivity. Cytologic and General health evaluations were made as well as Mucinou Precipitate quality. Synovial fluids was only collected from 40 horses in the GLC 5500RX test group as 10 horses opted out of this procedure and collections from control group were unnecessary to establish baseline parameters. Testing was compared to individual baseline to identify effects of treatment.

RESULTS—Bioavailability as determined by serum analysis for glucosamine, glycoprotein and chondroitin, GAG proved to be 63% in the GLC 5500 with the addition of embodiments of the present invention group compared to control. The relevant value (p<0.02) showed significant passage of the active ingredients through the digestive system and availability in serum. Significant improvement in all parameters of synovial fluid quality, volume, gross appearance, relative viscosity and mucinous precipitate quality were observed (p<0.006.) Most notably a steady increase in available Hylauronan was detected: base=0.5N, week 4=1.5N (2.0-4.0 mg/ml.), week 24=3.8 N (2.0-4.0 mg/ml.)

CONCLUSION and CLINICAL RELEVANCE—The application of GLC 5500 with the addition of embodiments of the present invention to the equines in this study showed significant improvement in TPF bioavailability providing a 63% of the total milligrams delivery to serum as compared to control. More importantly, previous clinical trials demonstrated the bioavailability of the original GLC 5500 without the addition of the embodiments of the present invention to be <30%. The new findings indicate that the addition of embodiments of the present invention more than doubles the bioavailability of TPF in this study and demonstrates a significant improvement in zeta potential and TPF survivability through the digestive system.

Significant improvements in intracellular absorption and utilization of TPF were also demonstrated. Synovial fluid markers showed dramatic improvement throughout the study indicating the application of GLC 5500 with the addition of embodiments of the present invention to the horses diet has a direct effect on synovial tissues. Specific increases in Hyaluronan count, volume and relative viscosity suggest that GLC 5500 with the addition of embodiments of the present invention has a direct modulatory effect on synovial TPF incorporation and may catalyze endogenous hyaluronan production. This may provide a viable non-invasive method for improving the health of equine synovial tissues. The combined findings indicate that GLC 5500 with the addition of embodiments of the present invention is an improvement on prior TPF delivery methods and may provide a superior modulatory effect over existing methods.

SUBHEADING-B, PROCEDURES—75 Equines were selected from a large population of high performance chronic joint pain/limited ROM sufferers. Inclusion criteria of study required lameness scores of at least 4 or higher for a minimum of 6-months prior to the start date of this study, determined by veterinarian. The subjects were randomized into two groups of subjects. The 50-subjects in Group A were provided GLC 5500 with the addition of embodiments of the present invention and administered 5.63 grams of the composition BID with regular feedings. (1-full scoop of product in the morning and 1-full scoop in the evening grain rations.) Subjects in Control Group B were fed normal rations without the addition of any secondary nutritional supplements or placebo to establish control. Blood, saliva and urine samples were collected and evaluated at baseline, and 4 week intervals thereafter. Lameness response to joint flexion, lameness grade, gross and histologic serum, saliva and urine biochemical data were compared using ANOVA and pair-wise t-testing between treatment groups to identify effects and safety of treatment, RESULTS—Statistical data analysis of joint pain frequency indicated significant differences between groups: Group A joint pain frequency was reduced by 48.7%. Group B joint pain frequency was increased by 20.5%. This increase in Group B can be attributed to the trainers and owners of these horses assuming they were on the live product and therefore attempting to increase their daily exercise program. Statistical data analysis of histological and biochemical data indicated significant differences between groups. The measurements that showed significant in-group change from baseline to finish were limited to Group A. Improvement in urine ORP p<0.01, pH p<0.01 and ST p<0.01 were all observed in Group A as compared to Control Group B. Blood serum analysis indicated improved ORP<0.01 and pH, p<0.01. Changes in blood ST were not significant as compared to baseline.

CONCLUSION and CLINICAL RELEVANCE—The application of GLC 5500 with the addition of embodiments of the present invention to the equines in this study showed significant improvement in equine joint pain and lameness as well as biochemical improvement in wellness parameters as compared to the control group. In addition no adverse side effects were recorded or reported throughout the span of the study. The resultant reduction in pain demonstrated through the daily administration of GLC 5500 with the addition of embodiments of the present invention, indicates efficacy as an oral treatment for equine lameness. Significant wellness changes in overall ORP and pH were seen at the cellular level indicating GLC 5500 with the addition of embodiments of the present invention may improve the production and utilization of energy, nutrient uptake and minimization of damaging free radicals. The findings suggest that GLC 5500 with the addition of embodiments of the present invention is safe for use in horses and may act to modulate the severity and progression of factors contributing to equine joint lameness through multiple biochemical pathways.

The findings of this study demonstrate embodiments of the present invention provide at least some of the following benefits: increasing TPF zeta potential, facilitating greater passage of TPF into the bloodstream, providing superior intracellular absorption and utilization of the TPF, and potentiating the therapeutic value of TPF systemically.

As discussed above, one of the primary challenges for their use as a dietary supplement has been survivability of the TPF through the digestive system. Until now it has been difficult to overcome metabolic hurdles that prevent TPF delivery to serum in high enough quantities to trigger the desired responses. Embodiments of the present invention beneficial enhance the bioavailability of TPFs such as, for example, three exogenous forms, Glucosamine HCl, Glucosamine NaCl and Glucosamine 2KCl. Other TPFs, for example can include Chondroitin Sulfate, exogenous protein/glycoprotein fractions, and amino acid isolates arginine, cysteine, glycine, glutamine, histidine, proline, serine and tyrosine.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

The invention claimed is:

1. A composition effective to increase the bioavailability of a target protein fraction in an herbivore, the composition per unit dosage comprising:
   about 750 mcg to 7.5 mg N-acetyl D-glucosamine;
   about 450 mcg to 4.5 mg Green *Chlorella*;
   about 188 mcg to 1.88 mg Licorice Root Extract; and
   about 10 mcg to 100 mcg Potassium Citrate.

2. The composition of claim 1, further comprising: (a) Zinc L-Carnosine; (b) Gamma-Oryzanol; and (c) Capsaicin.

3. The composition of claim 2, wherein the composition per unit dosage comprises:
   about 188 mcg to 1.88 mg Zinc L-Carnosine;
   about 600 mcg to 6 mg Gamma-Oryzanol; and
   about 10 mcg to 1 mg Capsaicin.

4. The composition of claim 1, further comprising: the target protein fraction.

5. The composition of claim 4, wherein the target protein fraction includes one or more of the following: glucosamine HCl, glucosamine NaCl, glucosamine 2KCl, and chondroitin sulfate.

6. The composition of claim 4, wherein the target protein fraction includes at least one of: glycoproteins, protein isolates, amino acids, glycosaminoglycans, and polysaccharides.

7. A composition effective to increase the bioavailability of a target protein fraction in a carnivore, the composition per unit dosage comprising:
   about 3 mg to 30 mg N-acetyl D-glucosamine;
   about 1.8 mg to 18 mg Green *Chlorella*;
   about 1.8 mg to 18 mg Licorice Root Extract; and
   about 20 mcg to 200 mcg Potassium Citrate.

8. The composition of claim 7, further comprising: (a) Zinc L-Carnosine; (b) Gamma-Oryzanol; and (c) Capsaicin.

9. The composition of claim 8, wherein the composition per unit dosage comprises:
   about 1.8 mg to 18 mg Zinc L-Carnosine;
   about 6 mg to 60 mg Gamma-Oryzanol; and
   about 400 mcg to 4 mg Capsaicin.

10. The composition of claim 7, further comprising: the target protein fraction.

11. The composition of claim 10, wherein the target protein fraction includes one or more of the following: glucosamine HCl, glucosamine NaCl, glucosamine 2KCl, and chondroitin sulfate.

12. The composition of claim 10, wherein the target protein fraction includes at least one of: glycoproteins, protein isolates, amino acids, glycosaminoglycans, and polysaccharides.

13. A composition effective to increase the bioavailability of a target protein fraction in an omnivore, the composition per unit dosage comprising:
   about 6.9 mg to 69 mg N-acetyl D-glucosamine;
   about 4.1 mg to 41 mg Green *Chlorella*;
   about 1.7 mg to 17 mg Licorice Root Extract; and
   about 46 mcg to 460 mcg Potassium Citrate.

14. The composition of claim 13, further comprising: (a) Zinc L-Carnosine; (b) Gamma-Oryzanol; and (c) Capsaicin.

15. The composition of claim 14, wherein the composition per unit dosage comprises:
   about 1.7 mg to 17 mg Zinc L-Carnosine;
   about 6 mg to 60 mg Gamma-Oryzanol; and
   about 10 mcg to 1 mg Capsaicin.

16. The composition of claim 13, further comprising: the target protein fraction.

17. The composition of claim 16, wherein the target protein fraction includes one or more of the following: glucosamine HCl, glucosamine NaCl, glucosamine 2KCl, and chondroitin sulfate.

18. The composition of claim 16, wherein the target protein fraction includes at least one of: glycoproteins, protein isolates, amino acids, glycosaminoglycans, and polysaccharides.

* * * * *